US 6,206,905 B1

(12) United States Patent
Holm et al.

(10) Patent No.: US 6,206,905 B1
(45) Date of Patent: Mar. 27, 2001

(54) DEVICES AND METHODS FOR APPLYING A MIXTURE OF TWO OR MORE LIQUID COMPONENTS TO FORM A BIOMATERIAL

(75) Inventors: Niels Erik Holm, Birkerød; Steven Linnebjerg, Skaevinge, both of (DK); Richard Cornwell, Deeside (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/358,078

(22) Filed: Jul. 21, 1999

Related U.S. Application Data

(62) Division of application No. 08/970,291, filed on Nov. 14, 1997.
(60) Provisional application No. 60/030,942, filed on Nov. 15, 1996.

(51) Int. Cl.[7] ................................................. A61B 17/08
(52) U.S. Cl. ............................................................ 606/214
(58) Field of Search ................................. 606/213, 214; 604/68–72, 82, 57, 191, 272, 225; 222/137, 135, 136

(56) References Cited

U.S. PATENT DOCUMENTS 5,887,755 * 3/1999 Hood, III .............................. 222/135

* cited by examiner

Primary Examiner—Michael Buiz
Assistant Examiner—(Vikki) Hoa B. Trinh
(74) Attorney, Agent, or Firm—Theodore R. Furman, Jr.; John M. Kilcoyne; Stuart E. Krieger

(57) ABSTRACT

Novel methods and devices which provide enhanced mixing and application of two liquid components to form a biomaterial with minimized aerosols is achieved using air flow rates below about 1.25 liters/minute in combination with a ratio of air flow to total liquid flow of from about 150:1 up to about 1500:1. Preferably the air flow is below about 1 liter/minute and the ratio of air flow to total liquid flow is from about 200:1 to about 1200:1. The parameters are ideally suited for the spray application of components which form a surgical sealant, e.g., a fibrin sealant. Also a part of the present invention are novel application methods for biomaterial, e.g., surgical sealant, components at liquid flows below 1.9 ml/minute, novel methods involving the mixing of such components on the exit surface of a spray tip or nozzle, novel spray tips and biomaterial applicators and methods for making such applicators.

7 Claims, 7 Drawing Sheets

Figure 1:
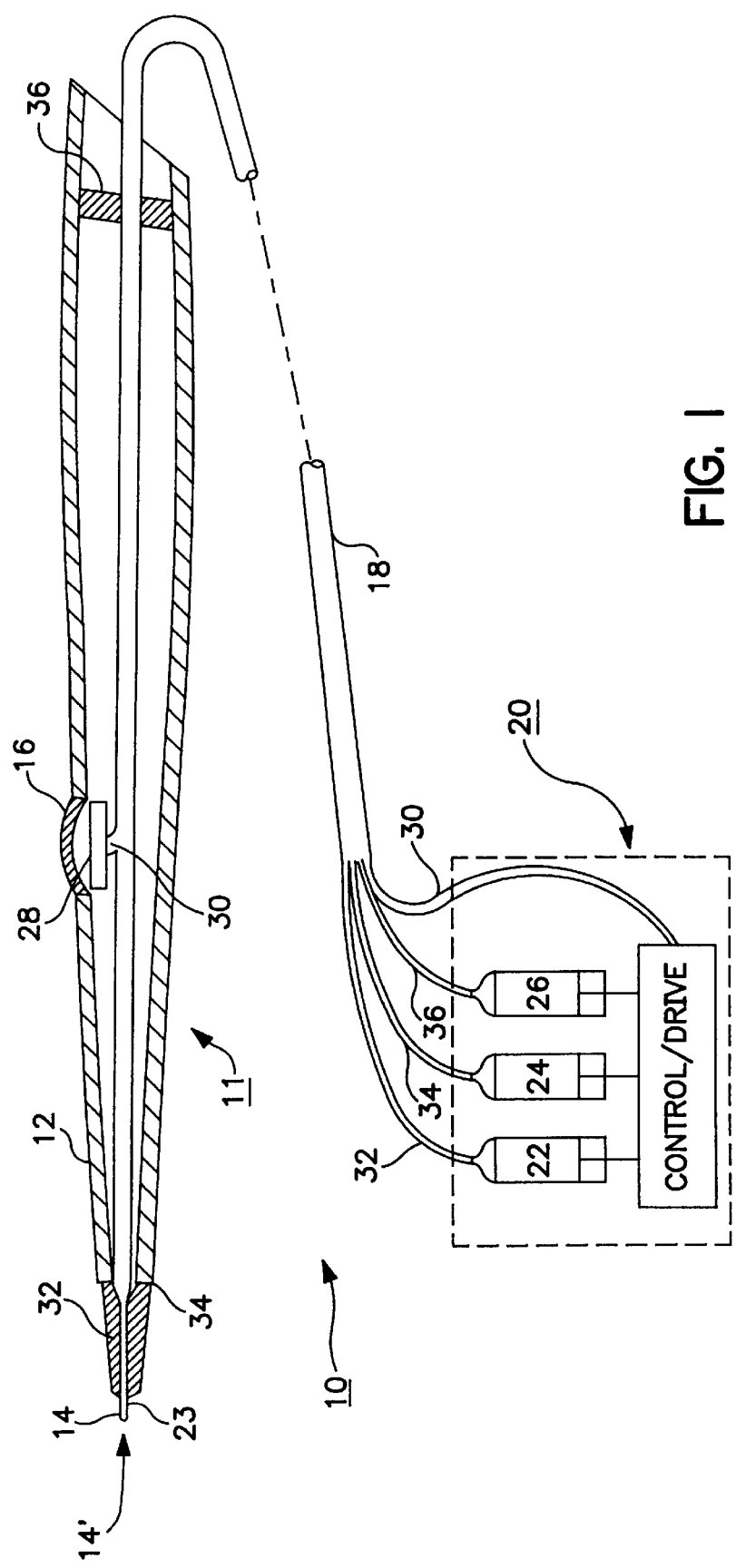

DEVICES AND METHODS FOR APPLYING A MIXTURE OF TWO OR MORE LIQUID COMPONENTS TO FORM A BIOMATERIAL

This is a Divisional of U.S. appl. Ser. No. 08/970291, filed Nov. 14, 1997 and claims priority to Provisional appl. No. 60/030942, filed Nov. 15, 1996.

TECHNICAL FIELD

The invention relates to a method of applying a mixture of at least two liquid components to form a biomaterial at a desired site and is more particularly concerned with the application of at least two components which will form surgical sealant, e.g., a fibrin sealant.

BACKGROUND ART

Numerous biomaterials, e.g., biopolymers, are utilized in the medical arena. Many of these are formed from the combination of two or more liquid components and can therefore be formed in situ by the co-application of such components. An example of this is a surgical sealant, e.g., a fibrin sealant, which can be formed by the co-application of a fibrinogen component and a thrombin component.

U.S. Pat. No. 4,359,049 to Redl discloses a double barrel syringe for applying a tissue adhesive such as fibrin glue or fibrin sealant to a human or animal in need thereof. The fibrin sealant described comprises predominantly two major components, a fibrinogen-containing component and a thrombin-containing component, each in liquid form upon use. Essentially, the thrombin and fibrinogen, when mixed, provide that the peptide chains of the fibrinogen are cleaved and conditions are provided so that the resulting fibrin polymerizes into a clot which is useful for sealing fluid and air leaks, in haemostasis and to connect tissue. To avoid premature clot formation double-barreled applicators are employed which, of course, keep the two components separate until application to a patient is required. The '049 patent discloses that pistons within the two cartridges, each containing one component, can be commonly actuated to dispense fluid simultaneously from each.

Other prior art patents describe various mixing methods for mixing two or more components used in these and other surgical sealants. For example, U.S. Pat. No. 5,116,315 assigned to Hemaedics describes a mixing head where the liquid conduits leading from the component cartridge enter a mixing chamber fashioned so as to provide a swirling of the components before they exit via a common exit channel. Adequate mixing of the components is desired so as to form a uniform fibrin sealant. Inefficient mixing results in the co-administration of fibrinogen and thrombin which may only result in a small yield of actual sealant. A difficulty with fibrin sealant applicators can be the premature formation of the clot within the device, especially those devices where the components are mixed within a mixing head and/or those devices wherein the components exit through a common channel. After the first spray of sealant is complete, a clot may block the exit channels rendering the applicator useless and greatly reducing the surgeon's flexibility in carrying out the sealant part of the surgical procedure.

U.S. Pat. No. 4,631,055 to Immuno includes a gas conveying channel for blowing a gas through the needle or mixing head during discharge of the components. However, an even, uniform distribution of the materials over the anatomical area of interest is still not achieved. Indeed, a significant amount of the components are wasted.

U.S. Pat. No. 5,605,541 discloses a device and a method of applying components of a fibrin sealant. The device comprises a source of a gas and a reservoir for each component wherein the gas source and each of said components are discharged through separate apertures. Preferably, the gas is discharged through the center aperture and the fibrin sealant forming components are discharged separately through each of the annular apertures.

European Patent 592,242 to Edwardson et al. discloses the first completely autologous fibrin sealant. It provides for the co-administration of a fibrin monomer solution with a buffer solution which provides for the polymerization of the fibrin monomer and can be prepared in less than 30 minutes from a single source of blood (preferably that of the patient to receive the sealant). This breakthrough technology provides a fixed amount of fibrin monomer solution from a sample of about 140 to 160 ml of blood. Uniform and efficient mixing is even more important in order to benefit from this safe, efficient, autologous sealant product and therefore new devices and methods for applying two or more components to form a surgical sealant are required.

Ideal application of fibrin sealants involves an efficient utilization of the sealant components to maximize coverage and effective use. Efficient utilization is accomplished by, inter alia, sufficient mixing of the components, uniformly controlled application of the components, the ability to apply the components intermittently and minimization of aerosols. It is also desirable for the surgeon to be able to vary the application rates according to the particular procedure and to be able to work in close proximity, i.e., less than 10 cm and even less than 5 cm, away from the tissue to be sprayed.

Among the parameters which can be most devastating to the performance of sealant applicators are mixing and clogging. Insufficient mixing results in the co-application of individual sealant components and only a portion of the amount of sealant desired is actually formed. This results in waste and poor sealant performance. Because the sealant components begin or continue the coagulation cycle upon mixing with each other there are limitations to the Hemaedics device described above and most current sealant applicators are designed to mix the components outside of the device to avoid clogging. Those skilled in the art can appreciate that proper mixing and application are difficult to control given that the important mixing of components occurs as they leave the device rather than inside the device. The characteristics of the applied sealant film are greatly impacted by the mixing/spray parameters and the fluid dynamics of the two liquids as they exit the device tip or nozzle. Clogging is often the result of the premature contact of the sealant components within the device, however, the handling and transfer of blood within plastic and/or glass tubing and appliances, generally, is inherently problematic, especially as inner device/tubing dimensions become smaller.

U.S. Pat. No. 5,582,596 to Fukunaga et al. discloses a spray applicator suitable for fibrin sealants which can be connected to a gas supply. Two liquid nozzles are located concentrically within two larger gas nozzles. The '596 patent states that the liquid nozzles protrude from the gas nozzle by from about 100 microns to 10 mm. The '596 patent also states that the liquid nozzles are from about 1.0 mm to about 20 mm apart. A commercially available applicator for Bolheal® sealant which appears to be an embodiment of the '596 patent actually has two liquid nozzles which protrude about 600 microns from the gas jets and which have inner diameters of about 625 microns wherein the liquid nozzles are on 3.0 mm centers or are about 2.4 mm apart. The product and '596 patent suggest that low pressures, e.g. 0.75 kg/cm² to 4.0 kg/cm² can be used but no mention is made of airflow, or sealant flow rates. Spray angles, aerosols and working distances for this device still leave room for improvement.

WO 97/20585 discloses a novel spray applicator for fibrin sealants which utilizes "in-line" apertures in the spray tip for expelling air (or other gas) and sealant components. That system uses relatively low air flow, i.e., 1.25 liters/min with sealant rates of nearly 2.0 ml/min to nearly 5.0 ml/min. The apertures in the spray tip are only about 300 microns in inner diameter and about 200 microns apart, i.e., on 5 micron centers. It is believed that this device is among the smallest in nozzle dimensions for blood, i.e., fibrin sealant application. Aerosols are considerably reduced and spray angles and mixing improved, but a finer controlled spray with even less aerosols and more efficient utilization of sealant components would be a useful addition to the art.

SUMMARY OF THE INVENTION

Figure 2:
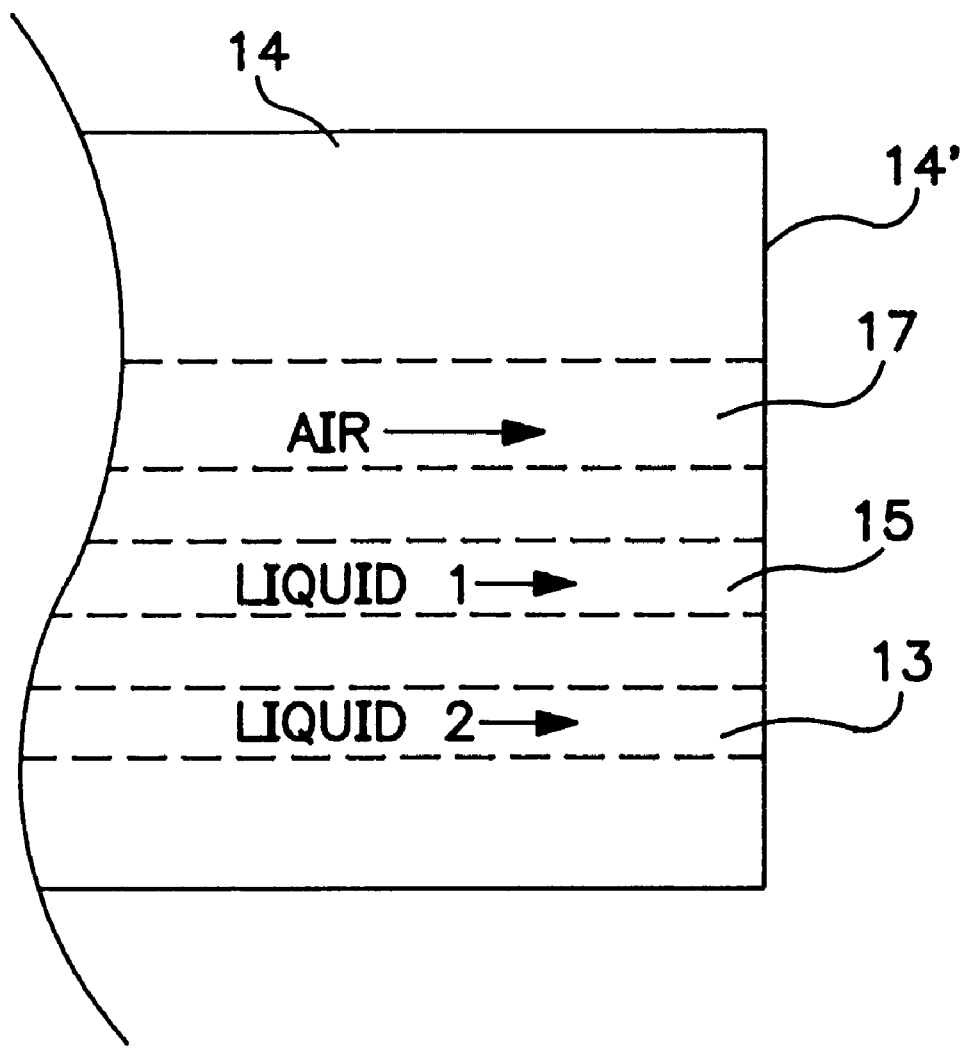
Figure 3:
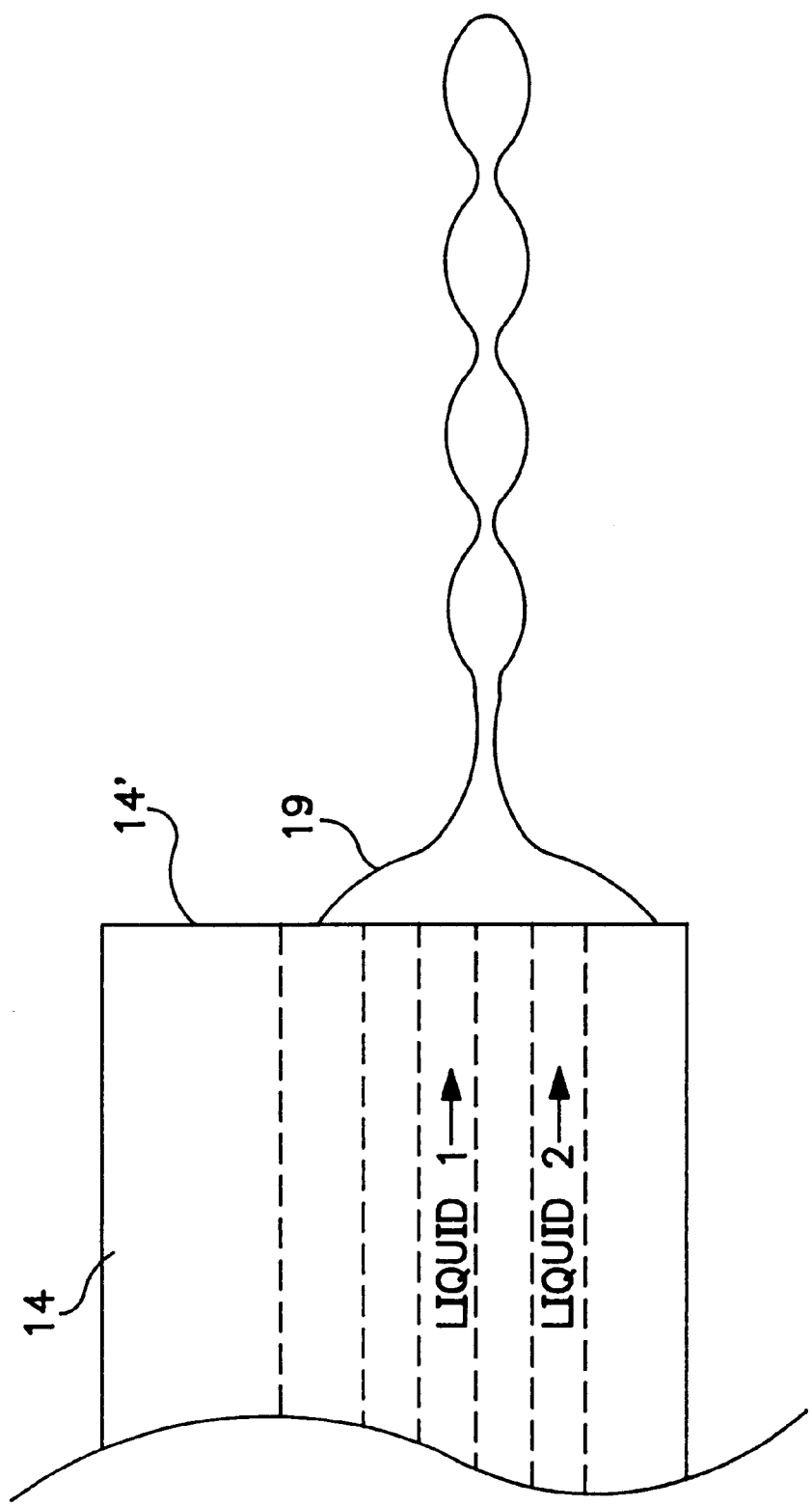
Figure 5:
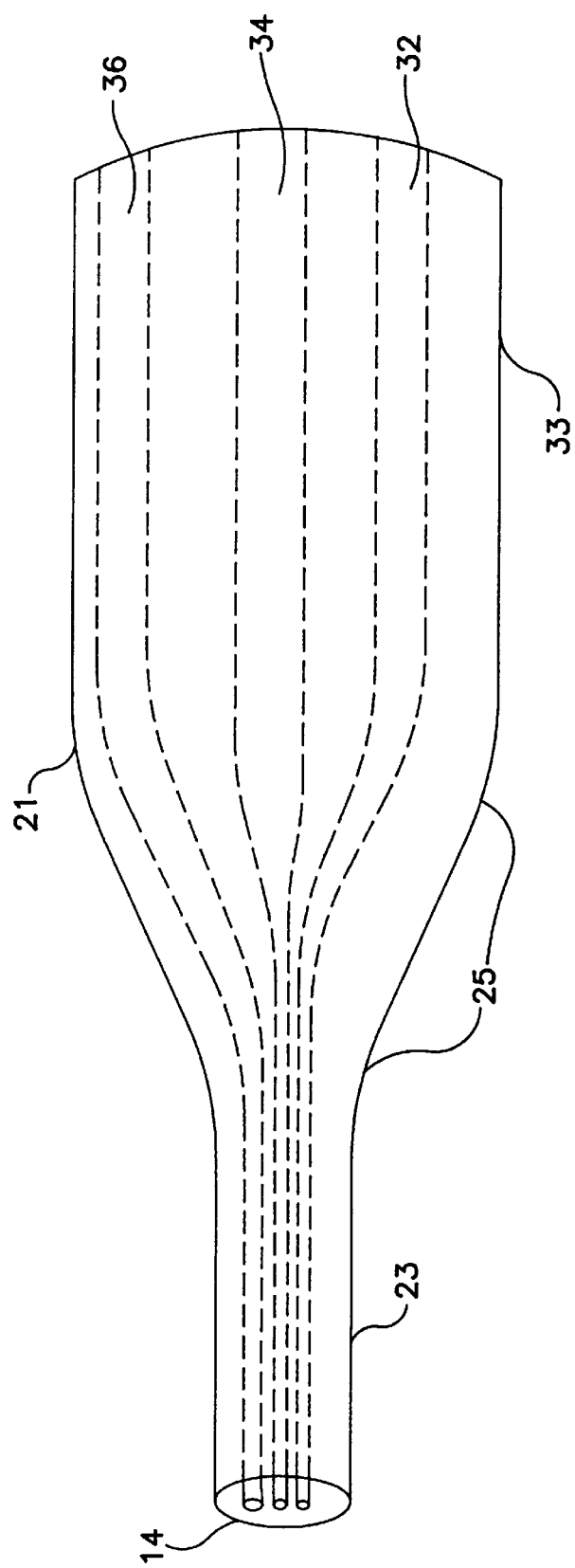

In accordance with the present invention it has been found that enhanced mixing and application of two liquid components to form a biomaterial with minimized aerosols is achieved using air flow rates below about 1.25 liters/minute in combination with a ratio of air flow to total liquid flow of from about 150:1 up to about 1500:1. Preferably the air flow is below about 1 liter/minute and the ratio of air flow to total liquid flow is from about 200:1 to about 1200:1. The parameters are ideally suited for the spray application of components which form a surgical sealant, e.g., a fibrin sealant. Also a part of the present invention are novel application methods for biomaterial, e.g., surgical sealant, components at liquid flows below 1.9 ml/minute, novel methods involving the mixing of such components on the exit surface of a spray tip or nozzle, novel spray tips and biomaterial applicators and methods for making such applicators.

BRIEF DESCRIPTION OF THE DRAWINGS

FIG. 1 is a lateral view of one embodiment of the application system of the present invention wherein the applicator is shown in partial cross-section.

FIG. 2 is a lateral view of the terminal end of a spray tip or nozzle of the present invention.

FIG. 3 is a lateral view of the terminal end of a spray tip or nozzle of the present invention showing the liquid mixing and flow without any spray gas.

FIG. 4 is a view similar to FIG. 3 but incorporating a spray gas.

FIG. 5 is a lateral view of the spray tip of the present invention.

FIGS. 6A and 6B are illustrations of the tip-forming method of the present invention.

FIGS. 7–9 illustrates various tip/aperture/lumen configurations of the present invention.

DETAILED DESCRIPTION OF THE PREFERRED EMBODIMENTS

The present invention provides for the enhanced application of two or more liquids for forming a biopolymer, e.g., a surgical sealant. The present device and methods provide uniform mixing at low air and liquid flow rates providing the capability to apply thin, even coats of sealant with reduced waste and aerosols. Examples of applications suitable for this new device and method are fibrin sealants wherein a gas, such as air, is used to help mix and apply two or more liquid components which could be a fibrinogen solution and a thrombin solution or a fibrin monomer solution and a fibrin-polymerizing solution, e.g., pH 10 buffer, as set forth in EP 592242 to Edwardson et al. As used herein, the term "total liquid/flow" or "liquid flow" or "sealant flow" refers to the combined liquid flow rates of the fibrinogen and thrombin solutions or of the fibrin monomer and fibrin polymerizing solutions. In addition to these liquid components other useful liquids or agents may be added and co-applied either with one or both of the above mentioned liquid components or via discrete pathways. For example, drugs can be co-applied, e.g., anticancer agents, antibiotics and other pharmaceutical agents as mentioned in EP 592242 or otherwise known in the art. Also, various types of cells can be co-applied which may be useful in the particular biomaterial employed. Further, liquids, polymers or other agents which can vary or control the texture or properties of the applied biomaterial can also be co-applied, e.g., hydrocolloids, alginates and other materials used adjunctively.

The application system can be any of those known in the art, e.g., the double-barrel syringes known to be useful for the delivery of surgical sealant in the prior art. The present invention is also suitable for incorporation into an application system similar in some ways to that described in WO 97/20585 and shown in FIG. 1. Accordingly, FIG. 1 shows an application system generally as 10 including an applicator 11 having an optional handle 12 with a spray tip or nozzle 14 and an optional actuator 16 to initiate application. The spray nozzle or tip 14 terminates in a generally flat lip surface 14' which is substantially normal to the longitudinal direction of the tip 14 and which includes exit apertures (not shown) through which gases and liquids are dispensed during application. The applicator 11 is in fluid communication via tubing means 18 with a source 20 of liquids and gases to be applied.

The present method employs a low air flow rate of below 1.25 liters/minute coupled with air flow rate to liquid flow rate ratios of 150:1 to 1500:1. Preferably, the air flow rate is below 1.0 liters/minute and the air flow:liquid flow ratio is from about 200:1 to about 1200:1. Most preferred ratios are between 400:1 and 1150:1. This provides that the total liquid flow rates are extremely low, i.e., below about 3.0 ml/minute and preferably below 1.9 ml/minute and even below 0.5 ml/minute but most preferably in the range of 0.5–1.5 ml/minute. Preferred gas flows are from about 500 ml/minute to about 800 ml/minute. These low air flow rates and low liquid flow rates provide excellent efficiency and control of the sealant application which is critical when considering that sealant procedures are typically undertaken with a fixed, i.e., limited, volume of sealant to be used in the surgery. Preferably the higher ratios are used with the higher gas flows and vice versa, as is illustrated in TABLE 1 of Example 1. In addition to a more efficient use of the sealant components, it is believed that multiple thin layers of sealant are more efficient than thicker, less efficient, poorly mixed masses of sealant components which may only partially interact to ultimately form the sealant.

It has further been found that proper mixing and application of the liquid components to form a biomaterial, e.g., a sealant is best accomplished in an applicator having a spray nozzle or tip with liquid and gas apertures of considerably smaller dimension and considerably closer in proximity to each other. Accordingly, a spray tip has been developed which has at least three apertures each of which has an inside diameter of less than 300 microns, where two apertures are for the liquid components which form the sealant and the third aperture provides the spray gas. A lateral view of such a spray tip 14 is shown in FIG. 2. Additional apertures may be provided for a second gas, additives or guide wires for endoscopic use. Preferably, the apertures for the liquid components have inside diameters of less than 250 microns and more preferably between 25 and 150 microns and most preferably between about 50 and 120 microns. The gas aperture can have the same inside diameter as the liquid apertures or preferably is about 20% to 50% larger in diameter than the liquid apertures when used in the present methods. Accordingly, in one preferred embodiment shown in FIG. 2 the spray tip surface 14' on the applicator has two 100 micron liquid apertures 13, 15 and a gas aperture 17 of about 140 to 150 microns in diameter. Preferably, the apertures are in a straight line and the gas aperture is at one end of that straight line as per WO 97/20585. If the liquids to be applied are delivered in other than a 1:1 ratio then it is preferable to have the liquid of the least amount exiting the aperture furthest from the gas aperture. In a preferred embodiment a fibrin monomer solution (pH4) and a buffer solution (pH10) are applied in a 7:1 ratio per the methods of EP 592242. In such a case it has been found to be desirable to have the pH10 exit from a first aperture, i.e., aperture 13 in FIG. 2, at one end of a line of three apertures, and to have the fibrin monomer solution exit from the middle aperture, i.e., aperture 15. This has been found to greatly enhance mixing of the liquid components when using the present devices and methods.

The mixing of the liquid components according to the present invention is related to the aperture size, the low liquid flow rates, the surface tension qualities of the biopolymer-forming liquids employed and the spacing between apertures. Accordingly, it has been found that when using absolutely no gas, at liquid flow rates below about 3.0 ml/minute and preferably at the lower end of the low liquid flow rates described herein, e.g., 0.5 ml/min–0.7 ml/min., that fibrin sealant-forming liquids will generally, due to their surface tension each form a droplet on the surface 14' of the spray tip 14 before that droplet departs from the spray tip due to the force of the liquid flow. That droplet is larger than the aperture diameter. This is easy to observe under low magnification and this approximate "droplet diameter" on the surface can be observed for various liquids. It has been found that superior mixing is provided when the spacing between the liquid apertures is such that these surface droplets will overlap or contact each other before being forced off of the spray tip towards the desired target. FIG. 3 shows the spray tip 14 with no air, but with the two liquids at low flow. The two liquids form a combined droplet 19 on the surface before the liquids (now mixed) are forced off of the spray tip 14 towards the target. In this regard, for fibrin sealant-forming liquids it has been found that the spacing between liquid apertures is preferably between 70% and 120% of the diameter of one aperture and preferably between 80 and 90% of the diameter of one aperture. That is, for a spray device having 100 micron liquid apertures, the edge-to-edge distance between those apertures should be between 70 and 120 microns and preferably the spacing should be between 80 and 100 microns. Looked at another way, in accordance with the preferred mixing methods of this invention a spray tip having 100 micron diameter liquid apertures ideally has those apertures at a center-to-center distance of between 120 microns and 220 microns and optimally between 130 and 200 microns. The gas aperture spacing from the adjacent liquid aperture is preferably in the same range as those spacings described above but may be identical to, or different than, the exact liquid-to-liquid spacing used.

During spray application, i.e., when the air or gas is utilized at the aforementioned flow rates of this invention in the aforementioned ratios of air flow to liquid flow of this invention, the droplet mixing at the surface of the spray tip serves as a premix of the liquid components before they are sucked into the air stream and broken up into smaller size droplets and further mixed during delivery to the desired site. This is illustrated in FIG. 4 where the combined droplet 19 can be seen being sucked into the air flow. Essentially the spray droplets being applied from the spray tip or nozzle form a cone shape as they approach the desired site. Cone angles for the present device and method are reasonably controllable according to the flow rates and spray distances selected. Spray angles attainable range from about 10° to about 40° and therefore provide reasonably reproducible widths of applied sealant as the applicator is moved laterally in a swath across a target area.

As mentioned above, the ideal spacing for the apertures on a spray tip or nozzle is determined without gas flow. This also gives way to a novel pinpoint sealant application method which is part of the present invention. Which is seen by referring back to FIG. 3. As mentioned above, the two liquid apertures are spaced such that the liquids form overlapping surface tension droplets forming a combined liquid droplet 19 on the surface 14' of the spray tip 14. At low liquid flow rates, i.e., preferably below 1.0 ml/min, these combined liquid droplets are forced off of the spray tip one or two at a time to provide a very uniformly mixed, controlled pinpoint, essentially dropwise application of surgical sealant. This application is preferred in certain instances where a focused applicator is required and large areas do not need to be covered, e.g., in certain nerve repair procedures.

Since the apertures in the present device are so small, it therefore follows that only a small area of each of the liquids is exposed to each other and to the outside environment. Accordingly, the tendency for the present spray tip to clog is greatly reduced. Further, the spray applicator of the present invention may be adapted so that the liquids are actually withdrawn a short distance back into the apertures upon discontinuing the spray or delivery mode as is explained in WO 97/20585. When the liquids are supplied from piston-driven cylinders via tubing means to the spray tip, this can be accomplished by withdrawing the pistons slightly. However, if the two sealant-forming liquids do remain on the tip surface of a spray applicator according to this invention, it has been found that the so-formed combined droplet (which may or may not begin to polymerize) either overlaps, or is in close enough proximity to the gas aperture that continuation or initiation of a gas flow alone readily removes the potentially clogging material. The gas flow used alone for this tip cleaning purpose can be any convenient flow either within or beyond the air flow rates otherwise utilized in this invention. Preferably, this tip-cleaning flow rate is the same as or up to 1.5 to 2.5 times greater than the gas flow being utilized for liquid spray delivery. In systems where the delivery of liquids and gas to the applicator are controlled, e.g., by a microprocessor as disclosed in WO 97/20585, it has been found useful to program an air flow into the procedure, where the air flow continues for a fixed period of time, e.g., up to about 30 seconds, after the application of liquid components. This "air only" cleaning step can also be programmed at the beginning of the application cycle.

As can be appreciated by those skilled in the art, forming a spray tip or nozzle of the dimensions prescribed by the present invention is a task of high precision. While injection molding such a spray tip may be possible, it is fraught with difficulties considering the dimensions involved. In accordance with the present invention, spray tips can be formed by the controlled heating and stretching of thermoplastic multilumen tubing where the tubing dimensions, prior to such heating/stretching, are actually several times larger than the desired tip dimensions. For example, low density polyethylene tubings are commercially available, e.g., from Putnam Co., as multilumen tubes having several lumens of the same or varied inside diameters. Unexpectedly, very small diameter tubings like these can be even further drawn and reduced without closing the lumens or destroying the basic shape of the tube, except for reducing the overall dimensions. FIG. 5 illustrates a spray tip 14 of the present invention which has been formed from a multilumen tubing 21. The multilumen tubing 21 has the spray tip 14 at the very end of the reduced tubing 23 which is integral with a transition portion 25. In the transition portion 25 the dimensions of the outside tubing and the interior lumens 27, 29, 31 transition from those of the reduced tubing 23 to those of the main tubing 33.

It has been found that multilumen tubing having 0.35 mm bore lumens can be carefully heated and drawn to reduce the dimensions, e.g., 3.5 times to provide 100 micron bores, 7 times to provide 50 micron bores and even 14 times to provide 25 micron bores. This remarkable finding provides an extremely cost effective way of preparing precision spray tips which would be virtually impossible to produce (at any cost) using conventional injection molding for thermoplastic materials. Further, it has surprisingly been found that blood components are readily deliverable at these dimensions without premature clotting or clogging problems.

Figure 6A:
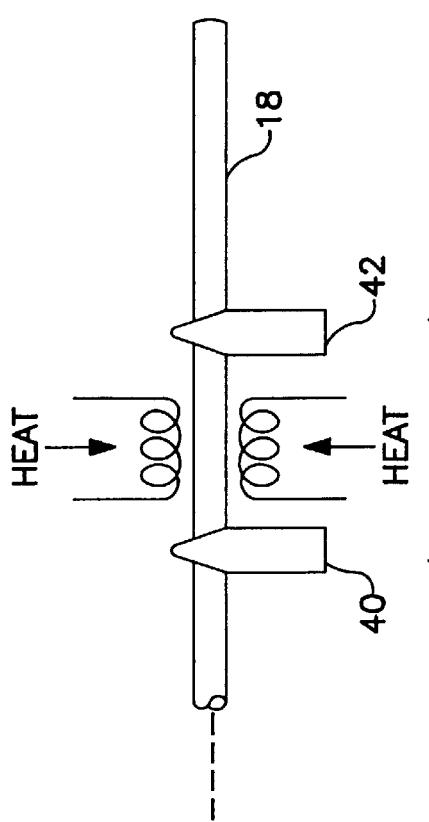
Figure 6B:
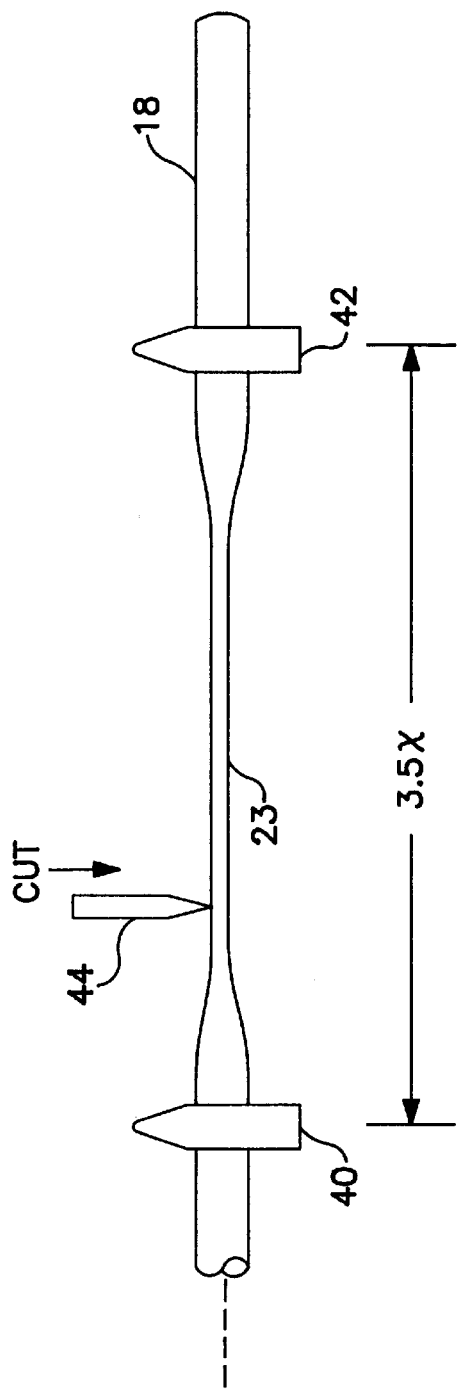

While the method referred to above and described in more detail below with reference to FIGS. 6A and 6B is preferred, any methods or technology suitable for fabricating these spray tips can be used. The spray tip can be of a thermoplastic material as described above or can be of a metal or ceramic material. Depending upon the material and dimensions chosen, known techniques such as molding, laser drilling electron discharge machinery (EDM) or spark erosion methods can be utilized to fabricate the present spray tip.

Figure 7:
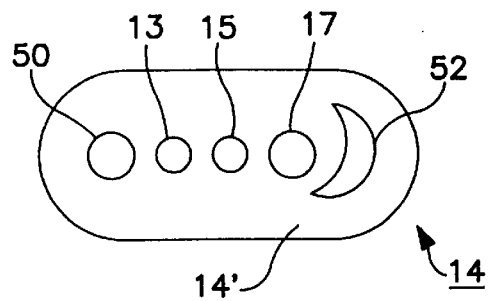
Figure 8A:
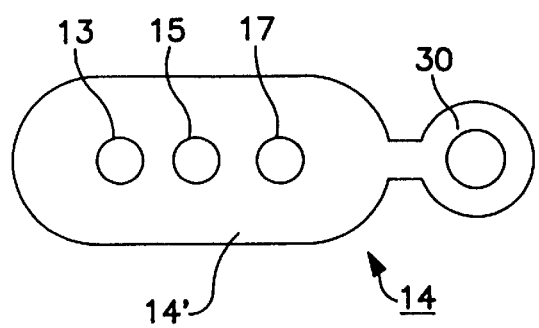
Figure 9:
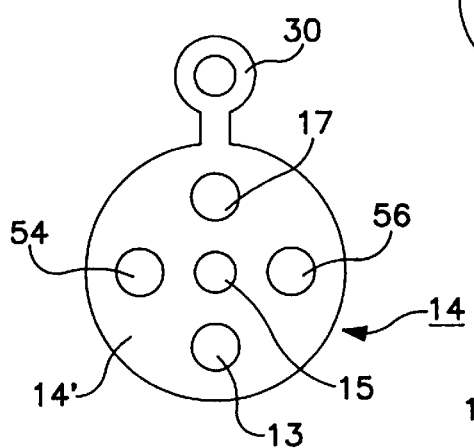

Further embodiments of the tubing and tip configurations which are part of the present invention are illustrated in FIGS. 7–9. FIG. 7 shows a spray tip 14 having a surface 14' with in-line apertures, i.e., gas aperture 17 and liquid apertures 13 and 15. Also shown are an auxiliary aperture 50 which can be used for additional liquids or gases, for additional reagents or excipients of for a guidewire for endoscopic purposes. Additionally auxiliary aperture 50 can merely be present to provide a desired stability or flexibility to the tubing itself. Crescent aperture 52 is a second gas aperture, i.e., in addition to gas aperture 17, which has been found useful in the tip-cleaning methods described hereinbelow.

Figure 8B:
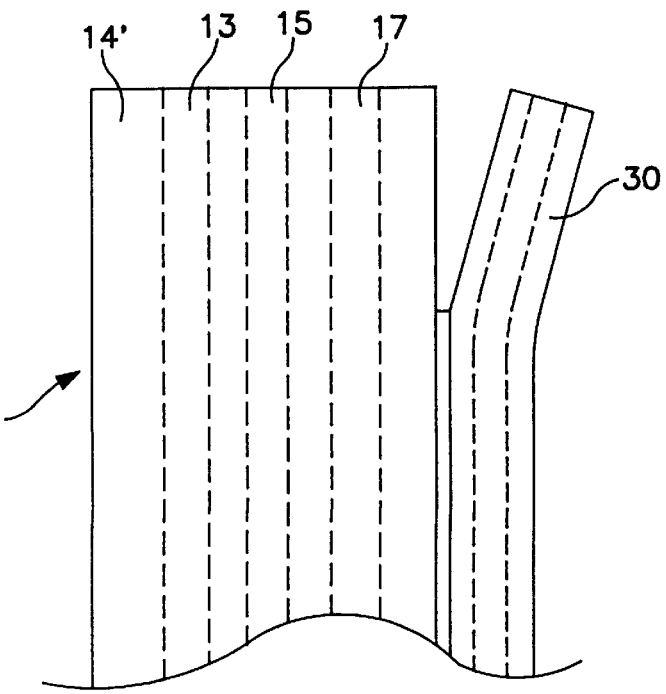

FIG. 8A shows a tubing cross-section with an integral, but separable, lumen 30 which can be used as shown in FIG. 1 as the actuator/pressure sensor tube 30. FIG. 8B shows a side view illustrating how the separable lumen 30 can be separated from the main lumen.

FIG. 9 shows a tip 14 with a surface 14' with three in-line apertures 13, 15 and 17 and a separable gas lumen 30 and auxiliary lumen 54, 56 which can be used for extra gas, extra liquid, reagents or excipients, endoscopic guide wire or simply to modify stability/flexibility of the tubing.

FIGS. 6A and 6B further illustrate the process for forming the novel spray tips of the present invention. A section of tubing 18 is held between a fixed clamp 40 and a slidable clamp 42. The principles described herein can be employed with any thermoplastic tubing and require some basic knowledge regarding the tubing material selected and the thermoplastic properties thereof. By way of example, a low density polyethylene 4-lumen tube from Putnam Company has an outside diameter of about 2.5 mm and four lumens having inside diameters of between 350 and 500 microns. As can be seen from FIG. 6A, sources of heat are applied to the area between the clamps. Applying the heat to a length of from 5 to 10 cm has been found useful but this will vary according to the desired shapes. The heat is applied until the tubing 18 begins to flow and can be drawn. For the exemplary tubing discussed herein about 280° C. is a sufficient heat source. When the tubing becomes liquid or pliable, the slidable clamp 42 is moved a pre-set distance. For example, if the distance X in FIG. 6A is 10 cm the clamp 42 can be drawn out so that the distance is 3.5 X or 35 cm, as shown in FIG. 6B. It has been found that this reduces the dimensions by about 3.5 times. Accordingly, in the center of the reduced tubing 23 the lumen inner diameters in FIG. 6A have been reduced from about 350 and 500 microns to about 100 and 150 microns, respectively. As shown in FIG. 6B a cutter 44 can be used to cut the tubing 18 and form the spray tip as desired. Further, referring back to FIG. 5 it can be appreciated that the tip 14 can be formed anywhere in the reduced tubing 23 or in the transition portion 25 according to the desired aperture size for the tip. It also appears from ongoing studies that a relationship between the diameters of the lumens in the main tubing 33 and in the tip 14 provide desirable spray qualities, ratios of 3:1 to 14:1 being found useful when the tip and tubing are of a single piece of material. Accordingly, cutting to form the tip 14 at a desired position along either the reduced tubing 23 or the transition position 25 serves not only to establish the aperture diameters but the ratio of those diameters in relationship to the lumen diameters in the main tubing 33.

Referring to FIGS. 5 and 6A, a measuring means (not shown) could also be employed in the tip-forming method described herein. Such a measuring means has the purpose of determining either the desired size or desired characteristics of the spray tip by measuring the inner diameters of the lumen or outer diameter of the tubing, either optically or mechanically. In this way, the cut to form the tip could be made in precisely the correct location along either the reduced tubing 23 or the transition portion 25. Alternatively, gas or liquid could be run through the tubing 18 during the cutting step so that a measuring means could continue moving the cutter up the reduced tubing 23 and/or transition portion 25 towards the main tubing 33 until the desired flows are sensed.

A preferred spray applicator according to the present invention comprises an integral, one-piece tubing and spray tip. That is, a multilumen tubing is modified at one end, as described above, to make a reduced spray tip and the main body of the multilumen tubing serves as tubing means to provide fluid communication from the sources of liquid components to the spray tip. Referring back to FIG. 1, essentially the multilumen tubing such as that illustrated in FIG. 5 serves as the tubing means 18, a first end of which connects to the sources of liquid 22, 24 and gas 26. At the second end of the tubing rather than connecting to a spray tip or nozzle, the tubing is formed into the spray tip or nozzle 14 as described herein. An optional handle 12, preferably with an actuator 16, can be positioned anywhere along the tubing 18, e.g., near the nozzle 14 end for maximum directional control by the surgeon or further back along the tubing 18 so that a length of tubing 18 and the spray tip 14 extend out from the handle 12 useful, for example, for endoscopic purposes. The actuator 16 illustrated in FIG. 1 is part of the disclosure of WO 97/20585. Essentially, beneath the actuator 16 which can be, e.g., a flexible membrane of an elastomeric material, is a pressure switch 28 which is connected to a sensing air or gas tube 30. The opposite end of the sensing air or gas tube 30 is also shown connected to the control/drive unit of the sources 20 of gas and air. Depressing the actuator 16 provides that a pressure differential is created in the sensing air or gas tube 30 which pressure differential is detected as a signal in the control/drive unit. In response to this signal the contents of the liquid sources 22 and 24 and the gas source 26 are delivered up the respective lumens 32, 34 and 36 through the tubing means 18 and out the apertures 13, 15, 17 (not shown in FIG. 1) of the spray tip 14. The sensing tubing 30 may be distinct from the tubing means 18 or may be integral with, but separable from, the tubing means 18 as shown in FIG. 1. The application system 10 of FIG. 1 may also include a retaining sleeve 32 which can be of a thermoplastic or elastomeric material and which provides a snug fit between the reduced tubing 23 and the nozzle end 34 of the handle 12. Also a grommet 36 may be included at the rear portion of the handle 12. The sleeve 32 and grommet 36 are added to provide stability to the tubing 18 and tip 14 while handling and using of the applicator 11 of the application system 10 of this invention. The handle 12 can be of any semi-rigid or rigid material and plastic materials used in the medical device field are useful in that they are light and easy to manufacture.

WO 97/20585 also discloses, as is illustrated in FIG. 1 herein, that the source, or expelling means as it is referred to in WO 97/20585, is preferably remote from said spray nozzle or tip such that the sources of liquid and gas components are not held in the hands of the surgeon. This provides that the tubing means/spray tip, with or without a handle, serves as the applicator in such an application system. As such, it can be appreciated that a much more sleek, easy-to-handle applicator is provided compared to the prior art. The source or expelling means herein is also microprocessor controllable. All of these features are part of preferred embodiment of the present invention. The various flow rates and ratios which are a part of this invention can be programmed into the control/drive part of the source so that the surgeon can select and even vary the flow rates and ratios according to the particular procedures and surgical needs at the time. It is also contemplated as part of this invention that the gas or air could be pulsed to provide desired spray/application characteristics. Further in accordance with this invention depressing the actuator can provide that 1) the delivery of the liquids and gas is "on" until a second depression of the actuator; or
2) the delivery of the liquids and gas is "on" while the actuator is depressed and "off" when the actuator is released; or
3) a metered amount of liquids and gas are dispensed each time the actuator is depressed.

The present invention will now be further described by the following Examples but should not be limited to the details described therein.

EXAMPLE 1

Mixing

This example is designed to assess the mixing of two liquid components applied to form a fibrin sealant using the methods and devices of the present invention. The mixing efficiency of the fibrin sealant disclosed by Edwardson et al. in EP 592242 is readily assessed since the two liquids are a pH4 fibrin monomer solution and a pH10 buffer designed to render the mixed solutions neutral which in turn provides for the polymerization of fibrin monomer to a fibrin polymer, i.e., a fibrin sealant. Therefore, by spraying these liquids onto pH paper the mixing can be observed.

Figure 4:
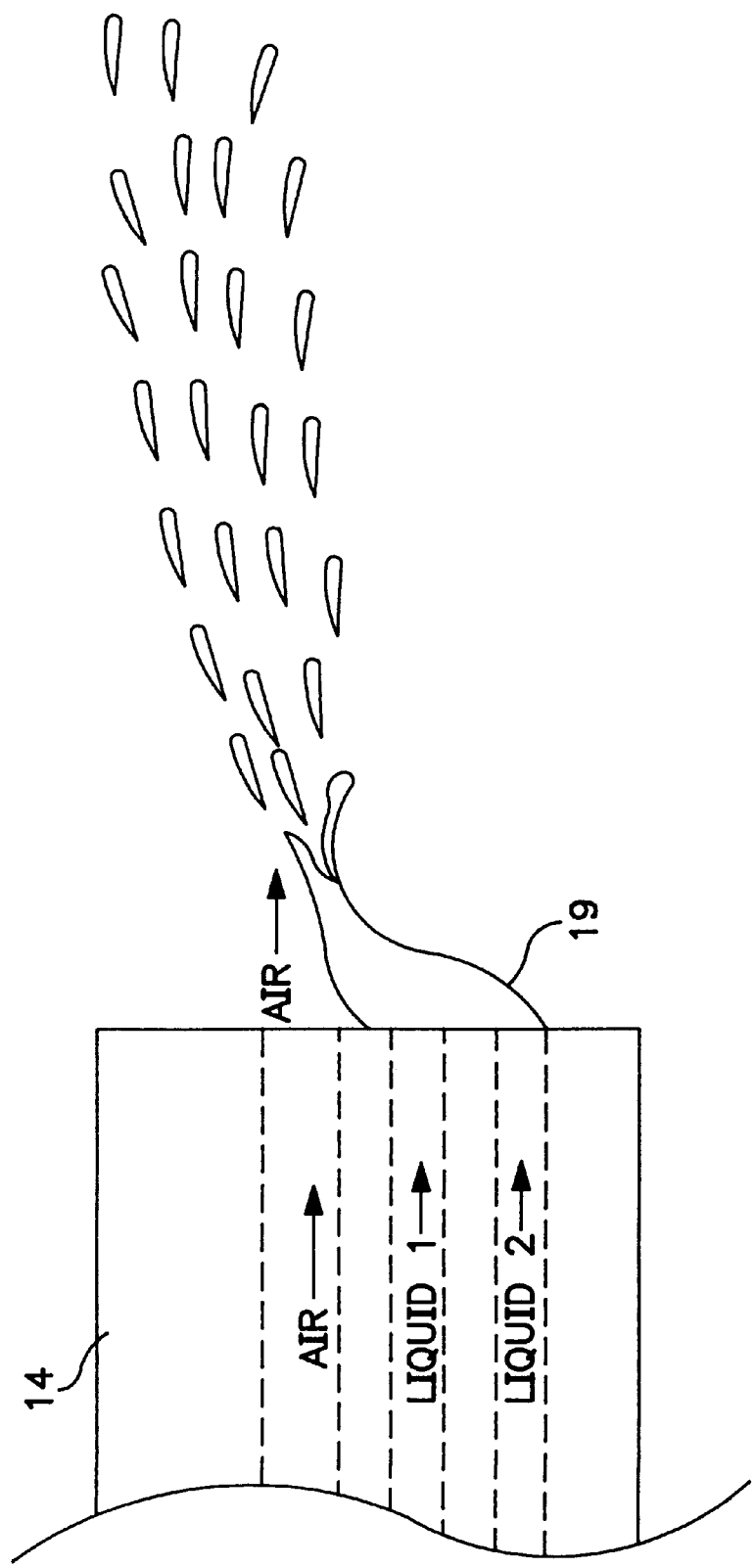

A spray applicator essentially as shown in FIGS. 1, 4 and 5 having a spray tip with two 100 micron diameter liquid apertures and a 150 micron diameter gas aperture. The apertures were arranged in a straight line with gas at one end, a fibrin monomer solution aperture in the middle and a pH10 buffer solution at the other end of the line of apertures. The apertures were approximately 90 microns apart (edge to edge).

A fibrin monomer solution was prepared as described by Edwardson et al. in EP 592242 and had a pH of 4. This was to be co-applied with a pH10 carbonate/bicarbonate buffer solution as also described in EP 592242 in a fibrin monomer to buffer ratio of 7:1.

These liquids were applied to a 20 cm$^2$ section of a full range (1 to 14) pH paper available from Whatman according to the parameters in TABLE 1 below. These spray parameters were also used in Example 2 which follows.

TABLE 1

| Test* | Liquid Flow | Air Flow | Air:Liquid | Spray Distance |
| --- | --- | --- | --- | --- |
| 1 | 0.7 ml/min* | 780 ml/min | 1114:1 | 10 cm |
| 2 | 1.4 ml/min** | 650 ml/min | 465:1 | 10 cm |
| 3 | 2.8 ml/min*** | 520 ml/min | 185:1 | 10 cm |
| 4 | 0.7 ml/min | 780 ml/min | 1114:1 | 5 cm |
| 5 | 1.4 ml/min | 650 ml/min | 465:1 | 5 cm |
| 6 | 2.8 ml/min | 520 ml/min | 185:1 | 5 cm |

*Low density spray = LD
**Medium density spray = MD
***High density spray = HD

The primary aim for these spray mixing experiments was to observe any spattering of non-neutral solutions caused by an incorrect mixing ratio or inefficient mixing or by blockage of either of the liquid apertures. A high portion of carbonate/bicarbonate buffer would be signified by blue spots of the pH paper, a high proportion of fibrin I solution would be signified by orange spots on the pH paper.

None of the applicators tested exhibited any incomplete mixing; the clots were always of neutral pH, signified by a green color on the pH paper. This observation suggests that the clots were well mixed. All samples taken were well mixed and the whole of the closest was at pH7.

EXAMPLE 2

The same device, liquids and spray parameters as set forth in Example 1 and TABLE 1 above, were employed in this experiment except as described herein. The fibrin monomer solutions used in this experiment were spiked with 20 µl of a 1% aqueous solution of rhodamine to make observation of the fibrin clots easier.

Applicators were held horizontally within a custom built rig at right angles and at a distance of 5 cm or 10 cm from a 20 cm$^2$ glass plate. A straight line point between application tip and glass plate was drawn on the plate. This point was to be the application target.

The spray was primed onto a shield placed in front of the target for a period of 5 seconds; the shield was then removed and the spraying continued, without pause, for a further 10 seconds onto the glass plate. The diameter of the resultant clot and also the distance of the clot from the target were noted. Any leakage, blockages or apparent deterioration of spray performance were noted.

The purpose of this Example 2 was to assess the spray diameters, spray direction and spray cone angles produced by applicators as described in Example 1. Ten applicators were run through the experiment described herein and the results are compiled in TABLE 2.

| SPRAY DENSITY | SPRAY DISTANCE | | | | | | | |
|---|---|---|---|---|---|---|---|---|
| | 5 cm | | | | 10 cm | | | |
| | LD | MD | HD | overall | LD | MD | HD | overall |
| Mea Diameter of Sealant | 2.8 cm | 3.2 cm | 3.2 cm | 3.1 cm | 3.4 cm | 3.9 cm | 4.1 cm | 3.8 cm |
| Mean Cone Angle | 30.9 | 35.5 | 34.9 | 33.8 | 19.0 | 21.8 | 23.1 | 21.3 |
| Direction-Distance from Target | 1.1 cm | 1.1 cm | 1.1 cm | 1.1 cm | 1.8 cm | 1.7 cm | 1.9 cm | 1.8 cm |

It can be seen that a fine, reproducible, variable, controllable spray is provided by the device and methods of the present invention.

What is claimed is:

1. A method for spray application of a fibrin sealant to a desired site by the simultaneous application of gas and at least two liquids which form said biomaterial upon mixing, which method comprises the steps of:

a) using an application system comprising separate sources of said gas and said liquids in fluid communication with a longitudinal spray tip via tubing, said spray tip having a flat outlet surface normal to said longitudinal direction, said tubing being connected to said sources and said tip, wherein said sources of gas and liquids are remote from said spray tip such that a user does not need to manually hold said sources while applying said fibrin sealant, wherein said tubing has a discrete channel for each of said liquids and said gas, each channel terminating at said flat outlet surface, and wherein said liquids include a fibrin monomer solution and a polymerizing liquid capable of polymerizing said fibrin monomer solution;

b) applying said liquids by the simultaneous transferring of said liquids and gas from said sources through said tubing to, and out of, said spray tip so that the liquids are mixed as they are applied to the desired site; and c) maintaining the gas flow below 1.25 liters/minute while maintaining the ratio of the gas flow to the total flow of the two or more liquids between 150:1 and 1500:1.

2. The method of claim 1 wherein the gas flow in step (c) is maintained at or below 1.0 liters/minute and the ratio of gas flow to total flow of the two or more liquids is between about 200:1 and 1200:1.

3. The method of claim 1 wherein the gas flow in step (c) is maintained between 500 and 800 ml/minute and the ratio of gas flow to total flow of the two or more liquids is between 450:1 and 1150:1.

4. The method of claim 1 wherein the higher gas flows are employed with the higher gas-to-liquid ratios and the lower gas flows are employed with the lower gas-to-liquid ratios.

5. The method of claim 1 wherein said fibrin monomer solution is at about pH4 and said polymerizing liquid is a pH10 buffer solution.

6. The method of claim 1 wherein the gas and liquid flow rates are selected from the group consisting of about 780 ml/minute of gas and about 0.7 ml/minute of total liquids, about 650 ml/minute of gas and about 1.4 ml/minute of total liquids, and about 520 ml/minute of gas and about 2.8 ml/minute of total liquids.

7. The method of claim 1 wherein said sources of liquids and gases include means for varying the respective flow rates of the liquids and the gases.

* * * * *